US012582518B2

(12) United States Patent
Straubinger et al.

(10) Patent No.: US 12,582,518 B2
(45) Date of Patent: Mar. 24, 2026

(54) HEART VALVE REPLACEMENT PROSTHESIS WITH VARIABLE SEALING FUNCTION

(71) Applicant: TRICARES SAS, Paris (FR)

(72) Inventors: Helmut Straubinger, Aschheim (DE); Coralie Marchand, Munich (DE)

(73) Assignee: TRICARES SAS, Paris (FR)

( * ) Notice: Subject to any disclaimer, the term of this patent is extended or adjusted under 35 U.S.C. 154(b) by 873 days.

(21) Appl. No.: 17/607,565

(22) PCT Filed: May 25, 2020

(86) PCT No.: PCT/EP2020/064431
§ 371 (c)(1),
(2) Date: Oct. 29, 2021

(87) PCT Pub. No.: WO2020/239686
PCT Pub. Date: Dec. 3, 2020

(65) Prior Publication Data
US 2022/0218469 A1 Jul. 14, 2022

(30) Foreign Application Priority Data
May 27, 2019 (EP) .................................... 19176833

(51) Int. Cl.
*A61F 2/24* (2006.01)

(52) U.S. Cl.
CPC .......... *A61F 2/2412* (2013.01); *A61F 2/2427* (2013.01); *A61F 2210/0004* (2013.01); *A61F 2250/0069* (2013.01)

(58) Field of Classification Search
CPC .................. A61F 2/2409; A61F 2/2412; A61F 2210/0004; A61F 2/2427; A61F 2250/0069
See application file for complete search history.

(56) References Cited

U.S. PATENT DOCUMENTS 3,825,957 A * 7/1974 Kaster ................... A61F 2/2406
623/2.24
5,749,921 A 5/1998 Lenker et al.
5,840,081 A 11/1998 Andersen et al.
7,748,389 B2 7/2010 Salahieh et al.
(Continued)

FOREIGN PATENT DOCUMENTS

EP 2484309 A1 8/2012
EP 3071151 B2 7/2017
(Continued)

OTHER PUBLICATIONS

International Search Report and Written Opinion, Application No. PCT/EP2020/064431 dated Dec. 3, 2020.
(Continued)

*Primary Examiner* — Suzette J Gherbi
(74) *Attorney, Agent, or Firm* — The Dobrusin Law Firm, P.C.

(57) ABSTRACT
The disclosure relates to a heart valve prosthesis with a variable sealing function, a method for replacing a native heart valve with a heart valve replacement prosthesis with a variable sealing function and the use of a heart valve replacement prosthesis with a variable sealing function for treating a heart valve disorder.

15 Claims, 13 Drawing Sheets

101

102

Detail A

(56) References Cited

U.S. PATENT DOCUMENTS

| | | | |
|---|---|---|---|
| 8,070,800 B2 | 12/2011 | Lock et al. | |
| 9,782,256 B2 | 10/2017 | Zeng | |
| 10,039,639 B2 | 8/2018 | Marchand et al. | |
| 10,952,851 B2 | 3/2021 | Marchand | |
| 2004/0049207 A1 | 3/2004 | Goldfarb et al. | |
| 2004/0186563 A1 | 9/2004 | Lobbi | |
| 2005/0137697 A1 | 6/2005 | Salahieh | |
| 2006/0020327 A1 | 1/2006 | Lashinski | |
| 2006/0271166 A1 | 11/2006 | Thill et al. | |
| 2007/0005129 A1 | 1/2007 | Damm et al. | |
| 2007/0051620 A1 | 3/2007 | Visco et al. | |
| 2007/0142906 A1 | 6/2007 | Figulla et al. | |
| 2007/0244552 A1 | 10/2007 | Salahieh | |
| 2007/0270679 A1 | 11/2007 | Nguyen et al. | |
| 2008/0071361 A1 | 3/2008 | Tuval et al. | |
| 2008/0086107 A1 | 4/2008 | Roschak | |
| 2009/0005863 A1 | 1/2009 | Goetz | |
| 2009/0054976 A1 | 2/2009 | Tuval et al. | |
| 2009/0198315 A1 | 8/2009 | Boudjemline | |
| 2009/0222082 A1 | 9/2009 | Lock et al. | |
| 2010/0022948 A1 | 1/2010 | Wilson et al. | |
| 2010/0256754 A1 | 10/2010 | Styre | |
| 2010/0262231 A1 | 10/2010 | Tucal et al. | |
| 2010/0292779 A1 | 11/2010 | Straubinger et al. | |
| 2011/0029072 A1 | 2/2011 | Gabbay | |
| 2011/0046712 A1 | 2/2011 | Melsheimer et al. | |
| 2011/0160836 A1 | 6/2011 | Behen | |
| 2011/0208296 A1 | 8/2011 | Duffy et al. | |
| 2012/0083874 A1 | 4/2012 | Dale et al. | |
| 2012/0101571 A1 | 4/2012 | Thambar et al. | |
| 2012/0209122 A1 | 8/2012 | Garbini et al. | |
| 2013/0116779 A1 | 5/2013 | Weber | |
| 2013/0204357 A1 | 8/2013 | Thill et al. | |
| 2013/0274855 A1 | 10/2013 | Stante et al. | |
| 2013/0282110 A1 | 10/2013 | Schweich et al. | |
| 2013/0304200 A1 | 11/2013 | McLean et al. | |
| 2014/0144000 A1 | 5/2014 | Creaven et al. | |
| 2014/0155996 A1 | 6/2014 | Wilson et al. | |
| 2014/0214157 A1 | 7/2014 | Börtlein et al. | |
| 2014/0214159 A1* | 7/2014 | Vidlund | A61L 27/34 623/2.14 |
| 2014/0277409 A1* | 9/2014 | Bortlein | A61F 2/2418 623/2.11 |
| 2014/0303719 A1 | 10/2014 | Cox | |
| 2014/0331475 A1 | 11/2014 | Duffy et al. | |
| 2014/0350668 A1 | 11/2014 | Delaloye et al. | |
| 2015/0005811 A1 | 1/2015 | Lubock et al. | |
| 2015/0018938 A1 | 1/2015 | Von Segesser et al. | |
| 2015/0045881 A1 | 2/2015 | Lim | |
| 2015/0335421 A1 | 11/2015 | Figulla et al. | |
| 2015/0335429 A1 | 11/2015 | Morris et al. | |
| 2016/0015421 A1 | 1/2016 | Benning et al. | |
| 2016/0015516 A1* | 1/2016 | Bernstein | A61F 2/2412 623/1.1 |
| 2016/0058976 A1 | 3/2016 | Okamura | |
| 2016/0250051 A1 | 9/2016 | Lim et al. | |
| 2016/0354201 A1* | 12/2016 | Keogh | A61F 2/2418 |
| 2017/0056164 A1* | 3/2017 | Wang | A61F 2/844 |
| 2017/0290661 A1 | 10/2017 | Von Segesser | |
| 2018/0028310 A1* | 2/2018 | Gurovich | A61F 2/2418 |
| 2018/0049868 A1 | 2/2018 | Board et al. | |
| 2018/0325667 A1 | 11/2018 | Gallagher et al. | |
| 2019/0046314 A1 | 2/2019 | Levi et al. | |
| 2019/0053895 A1* | 2/2019 | Levi | A61F 2/2415 |
| 2020/0008941 A1 | 1/2020 | Stappenceck et al. | |
| 2020/0121454 A1 | 4/2020 | Spence | |
| 2020/0188102 A1 | 6/2020 | Marchand et al. | |
| 2020/0360141 A1 | 11/2020 | Stappenceck et al. | |
| 2021/0000593 A1 | 1/2021 | Rahmig et al. | |

FOREIGN PATENT DOCUMENTS

| | | | | |
|---|---|---|---|---|
| WO | 2001/064137 A1 | 9/2001 | | |
| WO | 2006/128185 A3 | 11/2006 | | |
| WO | 2008/118481 A2 | 10/2008 | | |
| WO | 2009/106545 A1 | 9/2009 | | |
| WO | 2009/137712 A1 | 11/2009 | | |
| WO | 2012/178115 A2 | 12/2012 | | |
| WO | 2013/104721 A1 | 7/2013 | | |
| WO | 2015/107226 A1 | 7/2015 | | |
| WO | 2016/090025 A1 | 6/2016 | | |
| WO | WO-2017151566 A1 * | 9/2017 | | A61F 2/2409 |
| WO | 2017/195125 A1 | 11/2017 | | |
| WO | 2020/049129 A1 | 3/2020 | | |
| WO | 2020/127372 A1 | 6/2020 | | |
| WO | 2020/157018 A1 | 8/2020 | | |

OTHER PUBLICATIONS

Nkomo, VT. et al., "Burden of valvular heart disease: a population-based study", The Lancet, (2006), vol. 368, pp. 1005-1011.

Mirabel, M. et al., "What are the characteristics of patients with severe, symptomatic, mitral regurgitation who are denied surgery", European Heart Journa/, (2007), vol. 28, pp. 1358-1365.

* cited by examiner

101

102

Detail A

Detail A

101

103

Detail B

Detail B

Detail C

Detail C

101

105

Detail D

Detail D 101     102

HEART VALVE REPLACEMENT PROSTHESIS WITH VARIABLE SEALING FUNCTION

CLAIM OF PRIORITY

This application is a national phase filing under 35 USC § 371 from PCT Application serial number PCT/EP2020/064431 filed on May 25, 2020 and claims priority therefrom. This application further claims priority from EP Patent Application EP 19176833.2 filed on May 27, 2019. The contents of PCT/EP2020/064431 and EP 19176833.2 are each incorporated by reference in its entirety.

FIELD

The disclosure relates to a heart valve prosthesis with a variable sealing function, a method for replacing a native heart valve with a heart valve replacement prosthesis with a variable sealing function and the use of a heart valve replacement prosthesis with a variable sealing function for treating a heart valve disorder.

BACKGROUND

Certain heart diseases, or disorders, or injuries, or malfunctions, or calcifications will lead to aortic, or pulmonary, or tricuspid or mitral insufficiencies, and consequently to enlargements of heart chambers, e.g. right or left ventricle for example caused by increased pressure values (hypertrophy). Such malfunctions and, or insufficiencies will lead to a further enlargement of one heart chamber as a compensation process for the leakage of the endogenous heart valve. A further enlargement of a heart chamber will lead to increased insufficiency. In case such a patient is not treated this continued process will be lethal for such a patient.

The above described malfunctions and insufficiencies can be cured by valve replacement devices with various known implantation techniques. Independent of the implantation techniques and independent of the implanted device, either a new heart valve, or a heart valve prosthesis, a sudden full functioning heart valve with no leakage at heart valve leaflets closure, may cause the risk of death.

Sudden sealing stops the leak from a high to a low pressure cavity. In the case of a mitral or tricuspid regurgitation at heart valve level, an abrupt sealing will increase the ventricular heart pump resistance during the ejection period (systole) because the blood will not leak anymore to a low pressure cavity (left or right atrial chamber).

The suddenly increased resistance requires higher cardiac power reserve. In patients with severe cardiac pump dysfunction, abrupt sealing may not be tolerated by a patient and my cause complications or even a cardiogenic shock.

A problem may arise in a heart valve repair or replacement due to the fact that a heart that has over years compensated the heart valve defect by hypertrophy and an increased pumping capacity is now working in the context of a healthy heart and it cannot immediately adapt to the corrected anatomy of full closing heart valves.

Hence, there exists a need for a heart valve replacement prosthesis which overcomes the disadvantages of known devices at least partially or essentially entirely or which represent an improvement of known devices.

Thus one object is to avoid an instant cause of valve tightness with regards to the pressure characteristics of the replacement heart valve.

Another object is a replacement heart valve having an allowance of leakage at the time of implantation as compared to a later time point after implantation, i.e. a replacement heart valve with increasing efficacy over a certain time window.

Another object is to provide a heart valve prosthesis wherein the prosthesis changes its flow dynamics or/and its prosthesis sealing behavior over time or during a certain time window or/and the valve behavior of the heart valve prosthesis over a certain time frame after implantation of the heart valve prosthesis.

Another object is a replacement heart valve wherein the sealing characteristics of the heart valve prosthesis will change within a certain time frame after implantation.

Another object is a replacement heart valve wherein the combination of the valve characteristics and the sealing characteristics of the heart valve prosthesis will change within a certain time frame after implantation.

Another object is a replacement heart valve wherein spacer, filter, tubes or other components can be attached to the replacement heart valve before implantation or during, or after implantation and can be minimally invasive removed any time after the implantation.

Another object is a replacement heart valve wherein spacer, filter, tubes or other components can be attached to the replacement heart valve before implantation or during, or after implantation and will disappear by biodegrading over time after the implantation.

Another object is a replacement heart valve wherein spacer, filter, tubes or other components can be attached to the replacement heart valve before implantation or during implantation and will disappear after medication over time after the implantation.

SUMMARY OF THE DISCLOSURE

In one aspect the disclosure relates to a replacement heart valve prosthesis comprising a frame, a replacement valve and a sealing means wherein the prosthesis has an inflow end and an outflow end and the inflow end and the outflow of the prosthesis form a conduit, and wherein the valve leaflets open when a fluid enters into the in inflow end to allow the fluid to flow through the conduit (forward direction/forward flow) and the valve closes when a fluid is pumped into the outflow end to prevent the fluid to flow through the conduit (reverse direction/back flow) characterized by a defined blood flow in the reverse direction/back flow when the valve leaflets are closing (the valve is closed).

In another aspect the disclosure relates to a method for the repair of a heart valve malfunction wherein the native heart valve is replaced by a heart valve replacement prosthesis as described herein, wherein the prosthesis is characterized by a defined blood flow in the reverse direction/back flow when the valve leaflet are closing (the valve is closed).

DETAILED DESCRIPTION OF THE DISCLOSURE

Figure 1A:
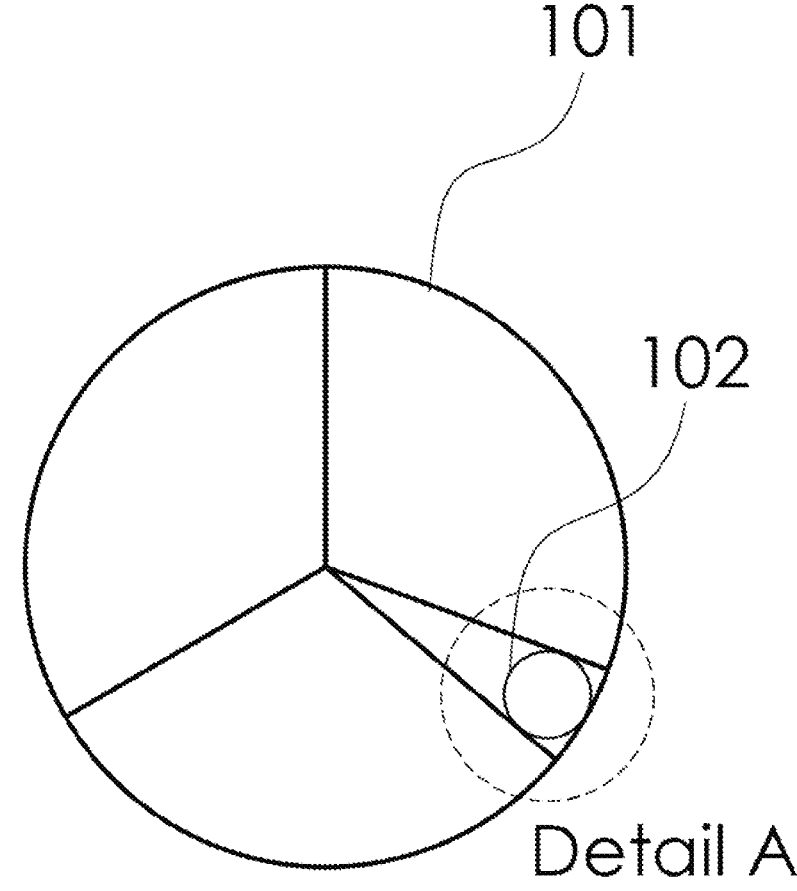
FIGS. 1A and 1B describe a heart valve prosthesis (101) according to the disclosure wherein a spacer (102) is positioned between two leaflets in order to prevent complete closure of the valve when the valve is in the closed position, e.g. the spacer (102) can be a balloon (as shown in FIG. 1B) or any suitable means which is useful for the defined prevention of complete closure; such a spacer (102) can e.g. also be made of a degradable material or a material and a design which allows its retrieval with a catheter based method. It will be appreciated by the skilled person that such a spacer (102) can also be designed so that it's diameter or dimensions are variably changeable in order to define the opening. The skilled person will appreciate that such a change may also be preset by way of a preset time window and a reduction in dimension or seize of the spacer (e.g. diameter or the diameter of the passage in the valve), e.g. over 1 to 12 weeks, or up to 8 weeks. It is also possible that the seize of the spacer can be modified by way of catheter manipulation wherein the dimension is reduced with a screw mechanism or a part of the spacer is taken out by way of a catheter procedure. In such a way the blood back flow can be varied according to the circumstances and needs in a particular case. Such a means can also be placed e.g. in the co-aptation zone of two valve leaflets of the heart valve prosthesis (101).
Figure 1B:
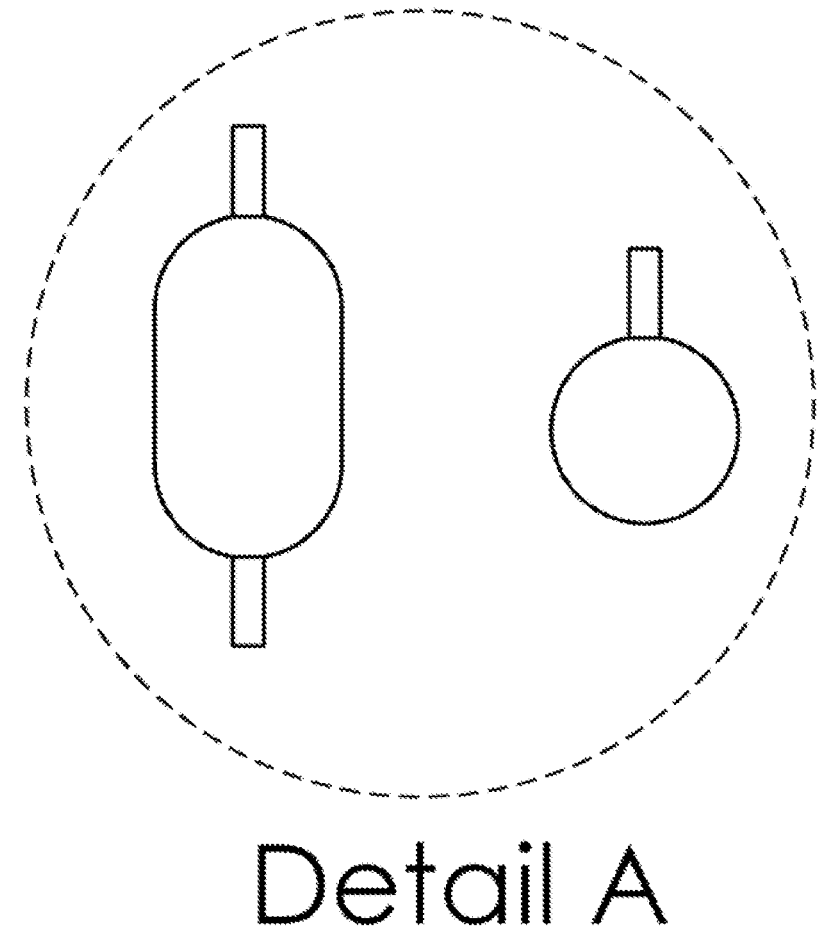
Figure 2A:
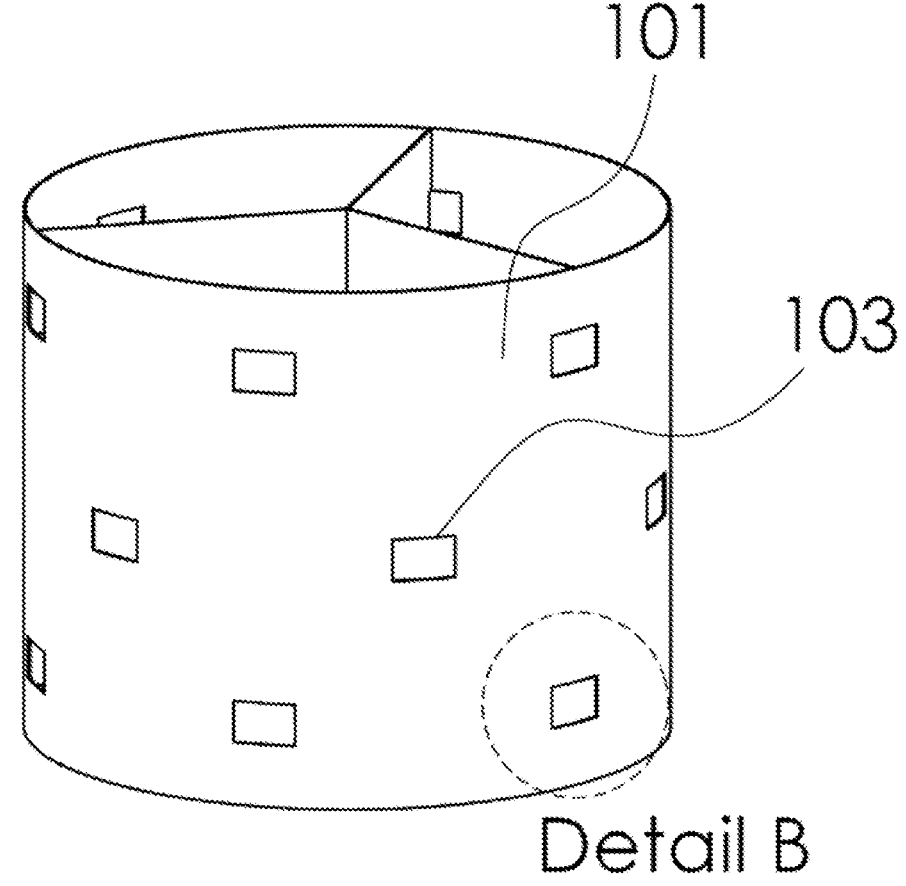
FIG. 2A describes means allowing for a blood back flow when a valve of a heart valve prosthesis (101) is in its closed position. Such means can be as shown in FIG. 2B (Detail B) designed e.g. as flaps (103).
Figure 2B:
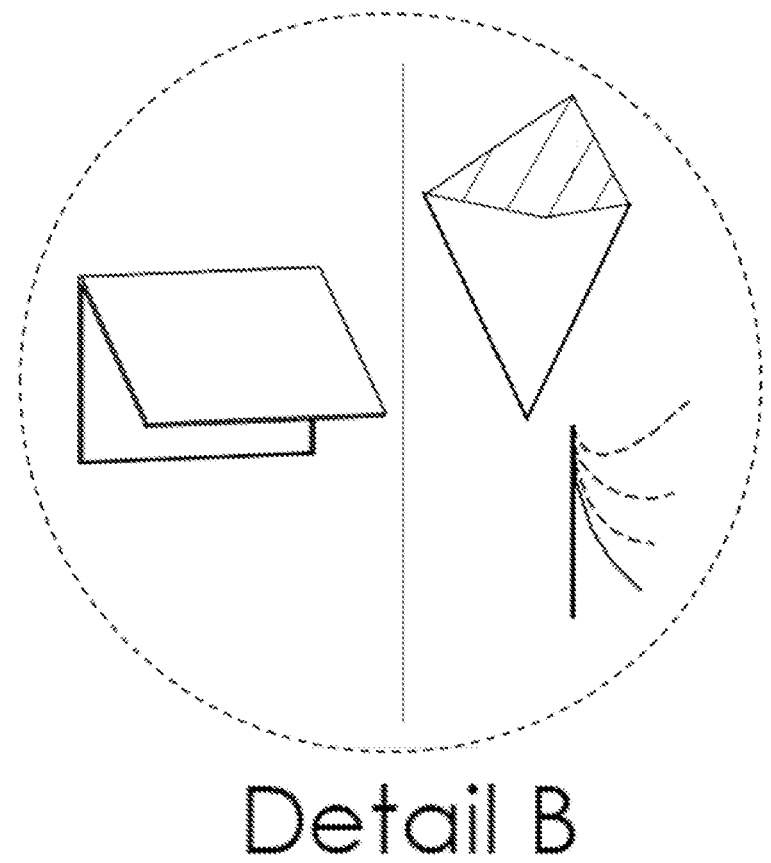
In FIG. 2B various possibilities of flaps are described. In particular a flap can be designed with a number of leaflets, e.g. 2, 3, 5 or 7. Any other feasible possibility as known by the skilled person can also be used to produce defined openings. The flaps can be placed in the covering or sealing of the heart valve prosthesis so that they allow the controlled blood back flow when the valve is in its closed position. It is also possible that the flaps can be closed over time by way of a net within the flap and wherein cells may attach and grow and close the flap or by way of a mechanical closure. Such a mechanical closure can be attached by e.g. minimally invasive techniques.
Figure 3A:
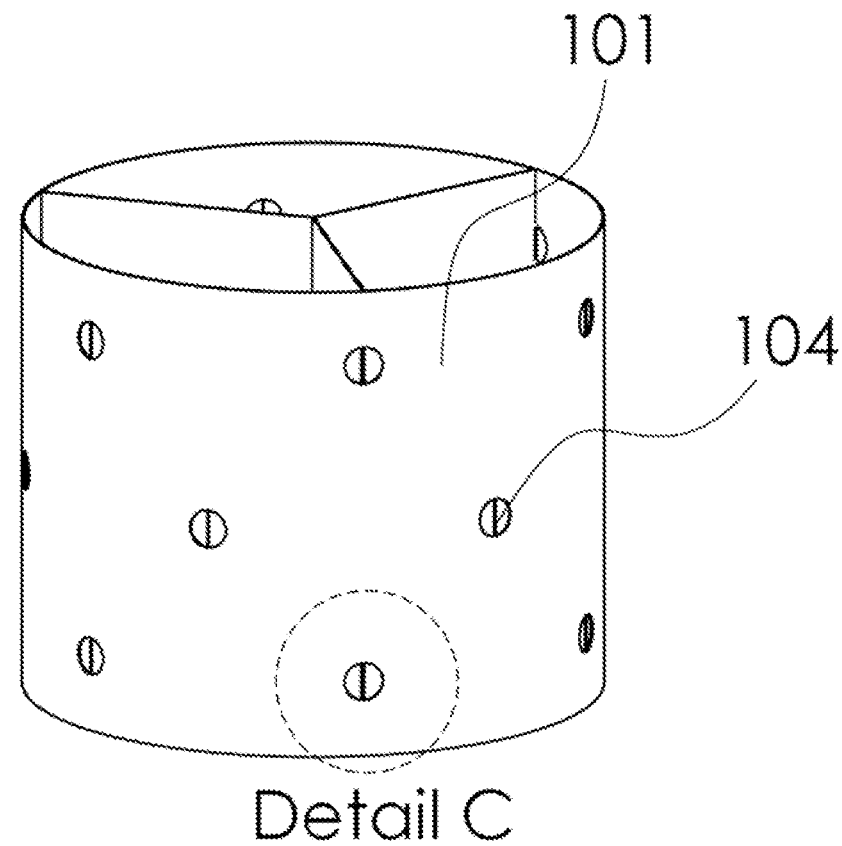
FIGS. 3A and 3B (Detail C) describe a variation of the disclosure of FIGS. 2A and 2B wherein filters or valves (104) are used to allow for a controlled blood back flow.
Figure 3B:
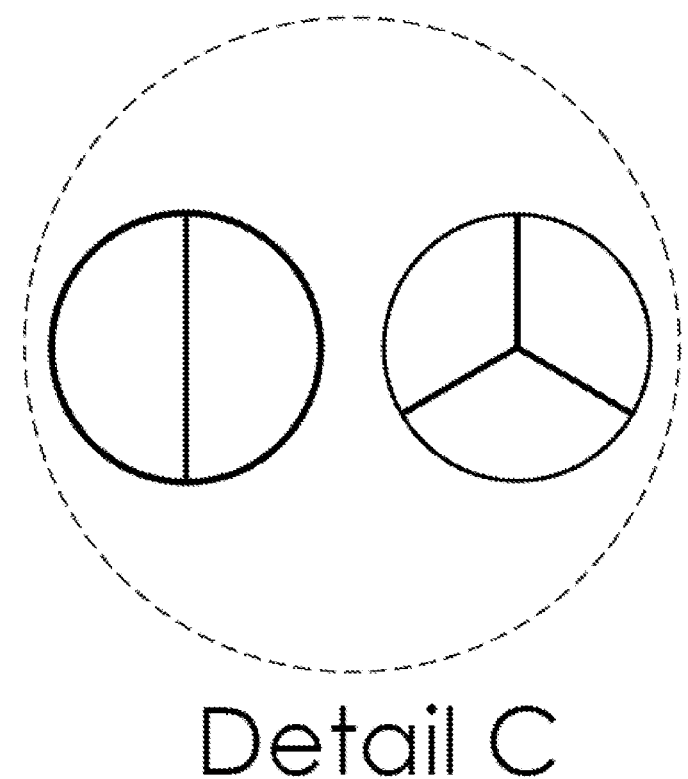
Figure 4A:
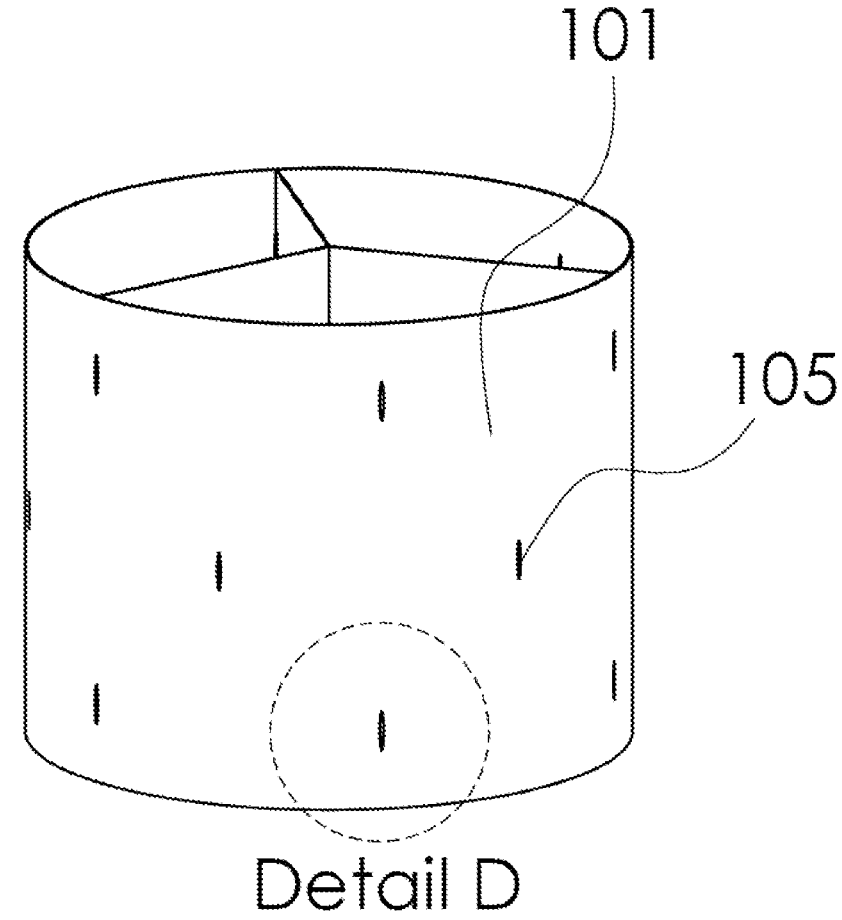
FIGS. 4A and 4B (Detail D) describe another variation of the disclosure of FIGS. 2A and 2B wherein cuts or slots (105) are used to allow for a controlled blood back flow. The cuts can be by way of a single line or a cross or star like manner.
Figure 4B:
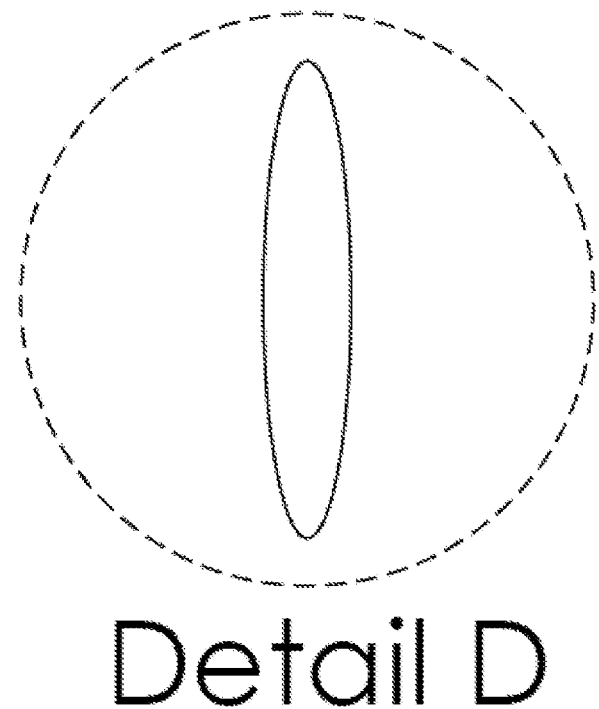
Figure 5:
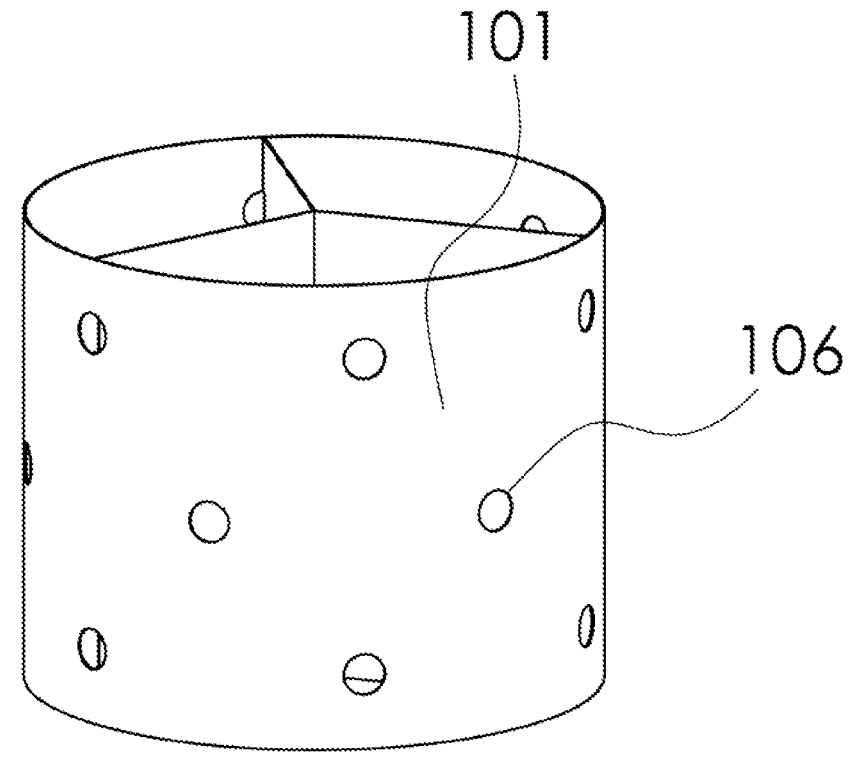
FIG. 5 describes another variation of the disclosure of FIGS. 2A and 2B wherein holes (106) are used to allow for a controlled blood back flow. The holes (106) will close over time by way of invasion of blood components and ingrowth of tissue fibers over a period of 1 to 12 weeks or up to 8 weeks post implantation and will thus close the holes essentially over time and slowly allow the heart to adapt to a finally tightly closing heart valve prosthesis. Thus advantageously the physiology of the individual receiving a heart valve prosthesis treatment can slowly adapt to the changing and correct or physiological pressure values during heart pumping.
Figure 6A:
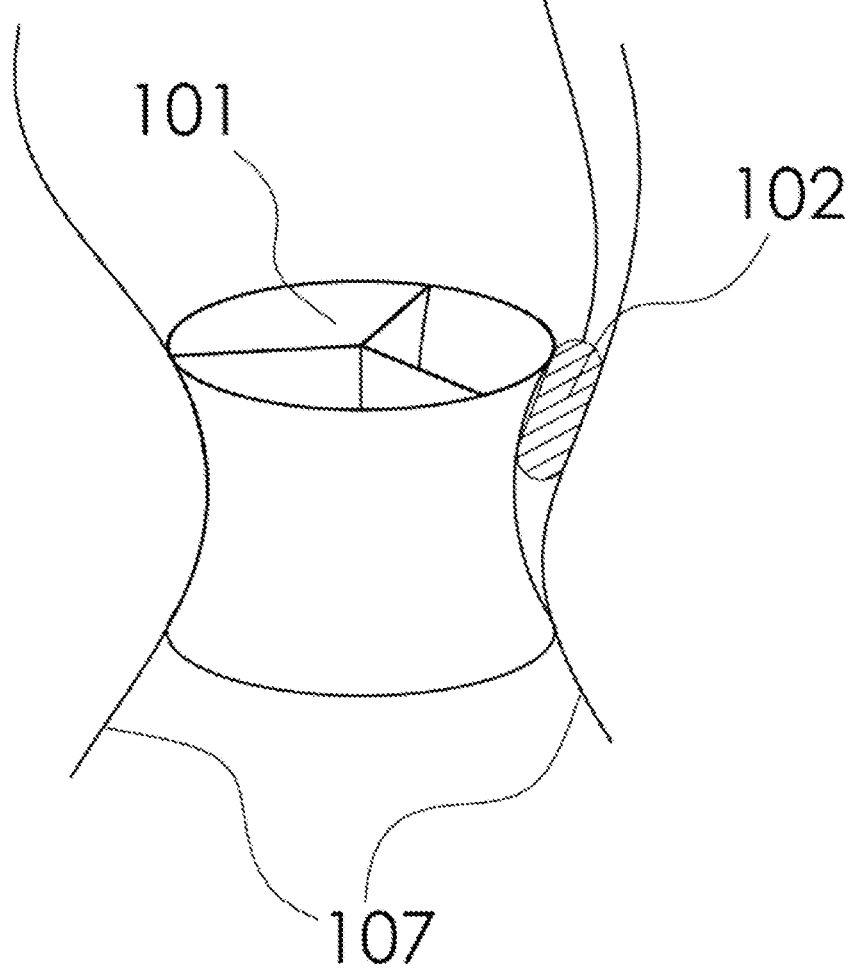
FIGS. 6A and 6B describe a spacer (102) according to the discposure, e.g. a balloon, which is positioned between the heart valve prosthesis and the surrounding heart muscle; the spacer (102) can be chosen from an appropriate seize and/or diameter adapted to the needs of the case. It can have a diameter of from 2 mm to 20 mm, or 1 mm to 50 mm. In a one example a balloon can be used which may be operable from the outside of the patient. Such a balloon can be connectable with a catheter for operation of the balloon.
Figure 6B:
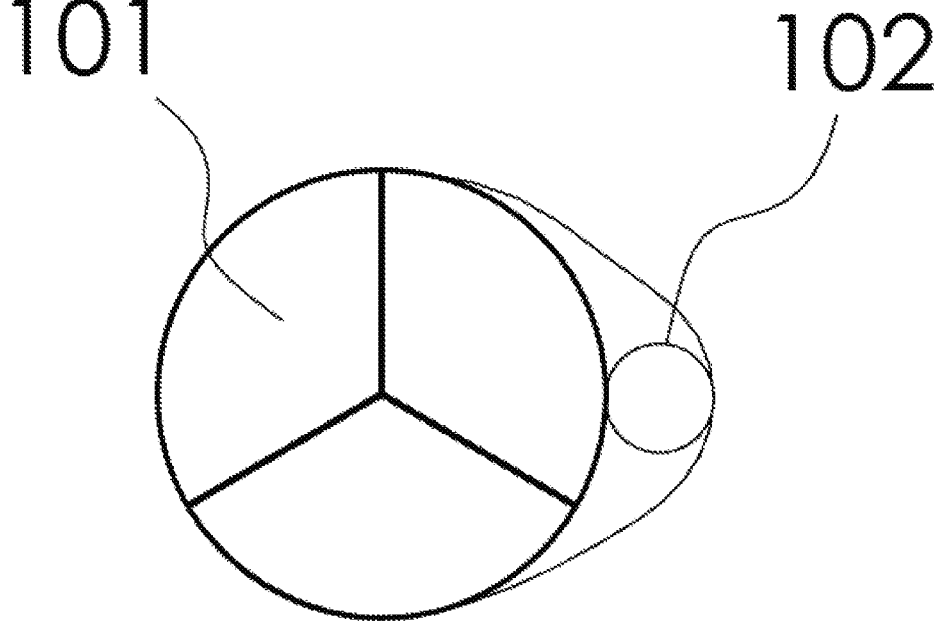
Figure 7A:
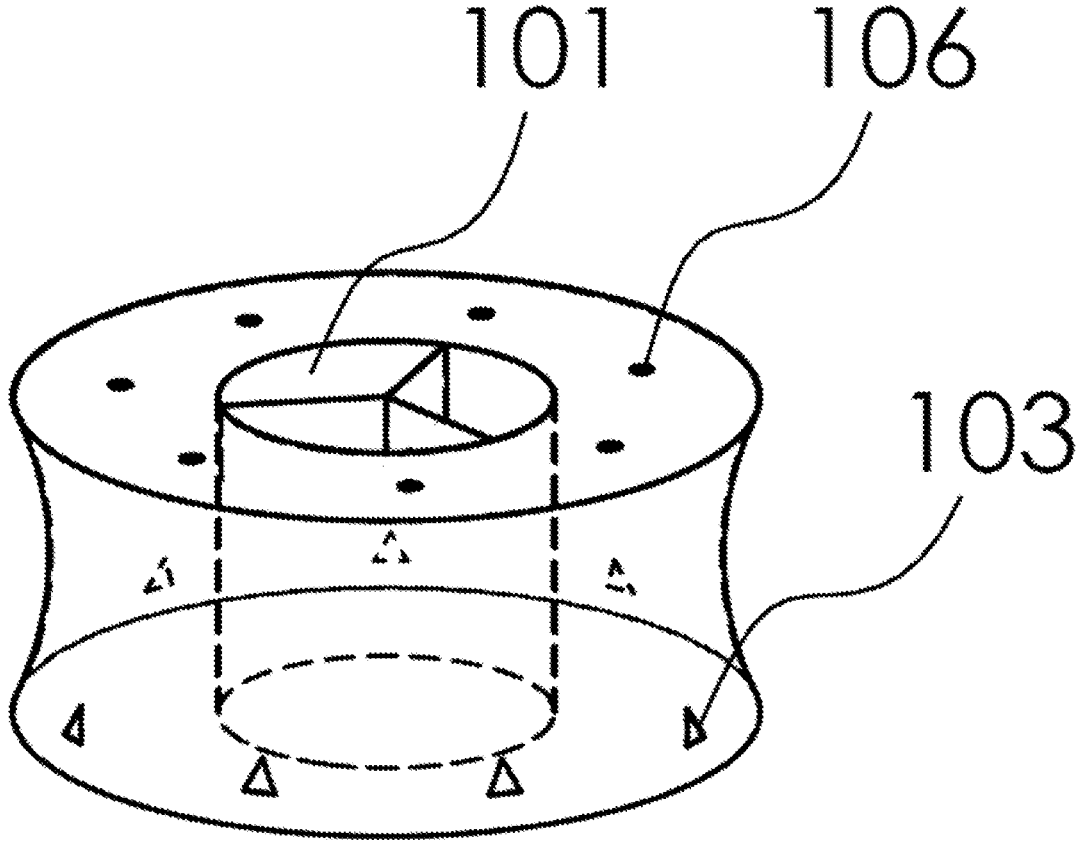
FIGS. 7A and 7B describe biodegradable means useful for introducing a controlled blood back flow during valve closure, e.g. a biodegradable ring (108). Such a means can be used to define and vary the diameter of the heart valve prosthesis outside the prosthesis, and thus a defined space between the heart valve prosthesis and the heart muscle or the annulus or the atrial or ventricular area at the implantation site can be created. The biodegradable ring (108) will be designed in order to define and calculate the time during which a defined blood back flow is allowed when the heart valve is in its closed position. The biodegradable ring (108) will degrade over a pre-defined period of time and thus reduce the space and opening, and over time the blood back flow will reduce and finally it will lead to an essentially complete sealing once the biodegradable ring (108) is essentially completely degraded. At that point the heart valve prosthesis is aligned essentially completely with the surrounding heart tissue. The time period for degradation will be chosen as is appropriate under the circumstances and advantageously for the patient. The degradation time frame can be from 1 weeks to 12 weeks or up to 8 weeks.
Figure 7B:
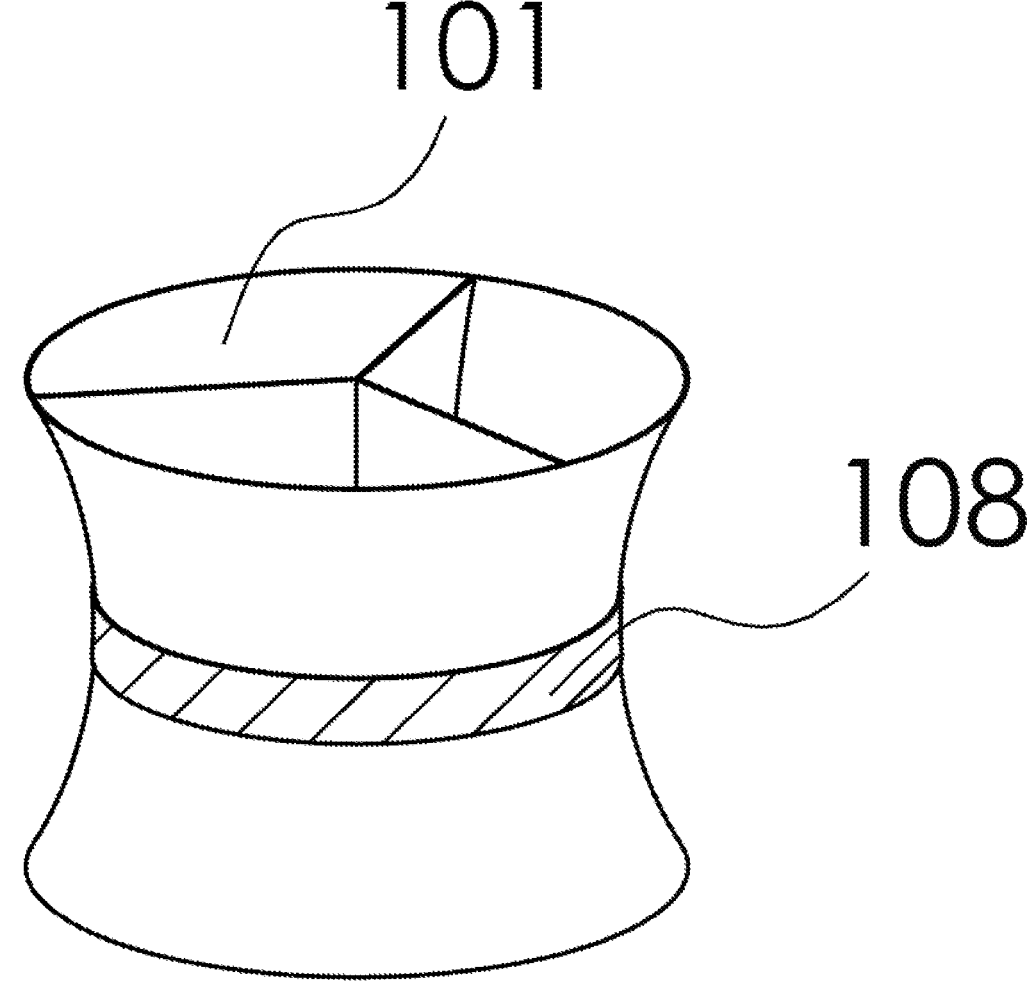

In the following certain terms of the disclosure will be defined. Otherwise technical terms in the context of the disclosure shall be understood as by the applicable skilled person.

The term "prosthesis" or "medical device" or "implant" in the sense of the disclosure is to be understood as any medical device that can be delivered in a minimally invasive fashion or by way of a catheter based procedure. The terms can be used interchangeably. A prosthesis in the sense of the disclosure can be e.g. a stent or stent-based prosthesis or stent-based heart valve prosthesis like an aortic heart valve prosthesis, a mitral heart valve prosthesis, a tricuspid heart valve prosthesis, or a pulmonary heart valve prosthesis. The prosthesis can be made of or comprise a stent in any known design like a mesh, braided, laser cut tube stent, or a stent composed of a single stent or multiple stent components. Such a prosthesis can be designed for delivery as a single piece or in a sequential way of delivery. The stent component(s) can also be combined with any other known materials and components known in the art like biocompatible materials etc.

The term "catheter" or "delivery device" in the sense of the disclosure is to be understood as a device used to deploy a prosthesis in a patient at a determined site, e.g. to replace a heart valve like a native aortic heart valve, mitral heart valve, pulmonary heart valve or tricuspid heart valve.

A "stent" in the sense of the disclosure can be any design of a stent and made of any suitable materials or cuts like a braided mesh stent or or a laser cut nitinol tube of one or multiple pieces. A stent in the sense of the disclosure can refer any known stent and/or prosthesis composed of one part or multiple parts, and/or it can be made of any suitable materials, as e.g. nitinol, and any material type, as e.g. a braided mesh or a laser cut material or any plastics, metal, composite materials etc. Examples of stents and prostheses are e.g. disclosed in WO2015/107226, PCT/EP2019/053633, EP18193122.1, EP19153905.5, WO2008/035337A2, WO2011/106532A1, WO2011/112706A2, U.S. Pat. No. 7,748,389B2 which are incorporated herein by reference.

A "stent area" or "stent areas" in the sense of the disclosure is a defined area of the stent or the heart valve prosthesis and in particular it is a longitudinal section or an outer section defined as proximal, middle or distal area or atrial, annular or ventricular or inflow, middle or outflow area. As described above the "inflow" and "outflow" definition of the prosthesis will depend on the particular native valve which is to be replaced.

An "inflow area", "middle area", "outflow area" in the sense of the disclosure denotes particular areas of the stent or prosthesis. Depending on the type of prosthesis and native heart valve to be replaced, the inflow area of the prosthesis will be positioned at the atrial or ventricular side and also the outflow area will be positioned respectively at the ventricular or atrial side of the native heart valve. The inflow area and the outflow area are connected by the middle area and constitute a tube for blood flow which will be blocked in one direction by a valve in said tube. The inflow area and outflow area are characterized by an inflow end and an outflow end, respectively, which may comprise additional features like anchors or fixation means, or a sealing etc. "Middle area" in a stent or prosthesis in the sense of the disclosure denotes the area between the inflow and outflow area.

An "annulus area" or "annular area" in the sense of the disclosure is either the respective area of an endogenous heart valve or it defines the respective area in the replacement heart valve or stent which is to be positioned at the implantation site and it meant to align with the endogenous annulus.

A "sub-annular area" in the sense of the disclosure is the area of the prosthesis which is located in the ventricle. Thus, again depending on the native valve it can denote the inflow or outflow of the prosthesis.

A "target site" or "target area" in the sense of the disclosure is the location or place where the replacement heart valve prosthesis is to be implanted and where a dysfunction or malfunction shall be treated, e.g. at the annulus of a tricuspid or mitral heart valve or any other valve.

A "defined leakage" and "defined paravalvular leakage" according to the disclosure is to achieve a defined blood back or backwards flow when the heart valve prosthesis is closed in order to define or avoid certain pressure differences in the heart after the implantation of a prosthesis and delivery of a heart valve prosthesis in order to replace native heart valves. Thus, the disclosure provides for means to a void a too severe change in the blood pressure during heart pumping right after implantation of a heart valve prosthesis. The disclosure thus provides advantageously and surprisingly for a smooth transition form the diseased state of a native heart valve to a cured status in such an individual and thus avoids partially or essentially entirely negative side effects due to the implantation of a heart valve prosthesis. In known devices the primary aim is to replace a malfunctioning or damaged native heart valve and to avoid immediately after implantation paravalvular leakage which however in certain disease states and in connection with certain native heart valve diseases, like e.g. in the mitral or tricuspid heart valve, may lead to serious side effects or serious issues for the individual receiving the heart valve prosthesis.

Thus the disclosure and the method as disclosed herein helps to avoid such negative impact on the individual after heart valve prosthesis implantation due to the tailoring of a gradual increase in blood flow pressure and blood pressure differences. The defined leakage can be engineered to be torrential, severe, moderate, mild, or trace. Depending on the severity of the malfunction or disease or disorder status of the individual one can achieve to avoid an essentially tight heart valve prosthesis by way of the means and measures as disclosed herein. For example one can design and chose the means for a controlled blood backflow in a manner that the leak tightness or blood back flow (paravalvular leakage or leakage within the valve of the heart valve prosthesis) is chosen to be at a level of severe, moderate, mild, or trace, in one aspect as moderate, mild or trace. The means, like spacer etc., as disclosed herein can be designed that over a time window of from 1 to 12 weeks, or up to 10, 8, or 6 weeks the blood back flow will gradually reduce and eventually arrive at an essentially tight status. One can design the development of such a gradually increase in tightness and reduction of blood back flow from stepwise e.g. from severe, moderate, mild to trace and essentially tight or in a more fast manner from severe to mild to trace or essentially tight. It is also possible that the degree of reduction in blood backflow will jump e.g. from torrential to severe or to moderate, or from severe to mild or to trace, or from moderate to mild or to trace or essentially tight.

The degree of blood back flow (blood backwards flow) can be measured with non-invasive means as known to the skilled person in heart surgery and cardiology. If necessary and depending on the particular embodiment of the disclosure one can adapt the degree of blood back flow at a certain time point after heart valve prosthesis implantation. Thus one can change the blood back flow from e.g. from torrential to severe or to moderate, or from severe to mild or to trace, or from moderate to mild or to trace or essentially tight. In another aspect of the disclosure the degree of change and of blood back flow will change automatically over time after the heart valve prosthesis implantation, e.g. over a time window of from 1 to 12 weeks, or up to 10, 8, or 6 weeks the blood back flow will gradually reduce and eventually arrive at an essentially tight status.

A "systolic back flow" or "systolic backwards flow" or "diasystolic back flow" or "diasystolic backwards flow" according to the disclosure is achieved by a "defined leakage" or/and "defined paravalvular leakage" wherein means are used that allow for a functional replacement heart valve prosthesis but allow for a defined back flow at the moment the valve should be in its closed position. Hence the systolic or diastolic backflow is, severe, moderate, mild, or trace. The same as pointed out above applies in this context with regards to blood back flow degree.

The term "closure of leakiness" or "reduction of leakiness" or "resealing" or "to achieve essential tightness" according to the disclosure relates to the process when a heart valve prosthesis was implanted into a subject which is characterized by a defined leakage or a defined paravalvular leakage and the leakage is reducing over time.

The means used to introduce a defined leakage should be closed over time either by an active process or by a passive process which is endogenous and based upon biology, e.g. by a thrombogenic reaction (passive). An active closure can be achieved by actively taking off spacers, etc. e.g. manually and minimal invasively. It is also possible that parts close automatically over time and thus achieve a resealing.

The leakage will essentially be reduced over time and thus the implanted replacement heart valve prosthesis will be essentially tight at the end of such a process and the subject's heart could adapt during this period to the now improved replacement heart valve functionality without provoking a too fast switch from a leaky dysfunctional valve to a essentially not leaky functioning heart valve. Such a closure can be foreseen as a development which is occuring over time after implantation or which is induced by specific means or/and minimally invasive manipulations.

A "back flow" or "blood back flow" or "backward flow" or "blood backwards flow" according to the disclosure relates to a blood flow in direction against the usual and natural blood flow through a native heart valve and the natural direction when the native heart valve is open.

A "biodegradable means" or "biodegradable ring" according to the disclosure relates to a means which one can position between a heart valve prosthesis and the implantation site in the area of the endogenous heart valve. Thus a defined conduit or leak can be produced to allow a defined amount of blood backwards flow when the valve of the heart valve prosthesis is closed. Such a biodegradable means can be any known material which degrades over time in a body of an individual. The biodegradable means can be chosen from any material which is biocompatible and biodegradable when implanted in an individual. It can be chosen e.g. from a synthetic (esters, amides, ethers, urethanes) or natural (polysaccharides and proteins) biodegradable polymer, e.g. polymers which degrade by hydrolysis like poly(lactic acid), poly(glycolic acid), poly(caprolactone), polyanhydride, poly (ortho ester), and polycyanoacrylate, or poly(amino acids) such as poly(L-lysine), poly(L-arginine), poly(L-aspartic acid), poly(L-glutamic acid), and poly[N-(2-hydroxyethyl)-L-glutamine] or from a chitin.

The invention is further described in more detail below.

The problem underlying the application is solved in one aspect by a replacement heart valve prosthesis comprising a frame, a replacement valve (valve) and sealing means wherein the prosthesis has an inflow end and an outflow end and the inflow part or area and the outflow part or area of the prosthesis form a conduit and wherein the valve leaflets open when a fluid enters into the in inflow part to allow the fluid to flow through the conduit (forward direction/forward flow) and the valve closes when a fluid gets pumped into the outflow end to prevent the fluid to flow through the conduit (reverse direction/back flow) characterized by a defined amount of blood back flow in the reverse direction/back flow when the valve leaflets of the prosthesis are closing (the valve is closed).

The defined amount of flow in the reverse direction/back flow (systolic or diastolic backflow) is one goal which is achieved with the device of the present disclosure in order to avoid in a diseased patient after implantation of a heart valve prosthesis that all of a sudden the heart and the organism of the patient is exposed to a situation wherein—in contrast to the status during the diseased status—the heart is exposed to a very different situation of pressure gradients during heart function. Thus a prosthesis of the current disclosure is advantageously a means to slowly adapt the patients heart and over time, i.e. the first days, weeks or months with a so called leaky valve (which exhibits reverse direction/back flow) which will eventually completely close and reduce its leakiness in order to provide for a essentially tight replacement heart valve which does not exhibit a backflow when closed.

In one embodiment the replacement heart valve prosthesis is characterized in that the defined amount of fluid flow in the reverse direction is predefined or it varies over time, e.g. it decreases or increases over a defined time frame, wherein the defined time frame is 1 day to 90 days or from 1 to 12 weeks or up to 10, 8, or 6 weeks.

The systolic or diastolic back flow can be defined as is required under the circumstances or/and depending on the target site and/or patient who will receive the replacement heart valve. The systolic or diastolic back flow can be achieved by various means and locations at the implantation site or within the replacement heart valve, e.g. the replacement heart valve leaflets themselves can be specifically designed to achieve a defined back flow or the sealing means and/or the contact areas between heart valve prosthesis and implantation site, e.g. at the sealing means or at the contact area itself as e.g. the annulus or in the atrium or ventricle area can be designed to comprise a leakiness and to allow for a defined back flow, preferably for a foreseeable time period after implantation.

It is possible that the heart valve prosthesis as disclosed herein is characterized in that the systolic or diastolic back flow into an atrium is 5 to 80%, or 20 to 40% of the outflow with limited closing of valve leaflets of the replacement heart valve prosthesis. The percentage of the leakage one can calculate e.g. based upon the blood flow in the correct blood flow direction.

In particular embodiments the replacement heart valve prosthesis as disclosed herein is characterized in that a back flow can be achieved by way of back flow means, wherein said back flow means are selected from the group consisting of active opening means (filters, flaps, spacers, valves), passive opening means (holes, cuts, openings) located at any surface of the prosthesis. One can e.g. position one or more filters, flaps, valves, holes, cuts or/and openings in the valve leaflets of the heart valve prosthesis, or in the sealing material which surrounds the outer part of the heart valve prosthesis, or a covering at one or either side towards the atrium or ventricle of the heart valve prosthesis. The number can vary between 2 and 30, e.g. it can be 6, 8, 10, 12, 14, 16, 18, 20 and it will be adapted as necessary to define the amount of blood back flow.

In another variation of the disclosure the means for defining the amount of blood back flow one can use a means which is attached or combined with the outside of the heart valve prosthesis. It can be a space, a balloon, or a biodegradable means, like a ring or one or more objects in a geometry to produce a space between the heart valve prosthesis and the target tissue like the annulus or/and the heart tissue in general. One can choose several rings (e.g. 2, 3, 4) around the heart valve prosthesis or other means which are positioned at one level or several levels on the outside of the heart valve prosthesis.

In other or combined embodiments a replacement heart valve prosthesis as disclosed herein can be characterized in that a back flow can be achieved by way of back flow means, wherein said back flow means are selected from biodegradable materials, or materials changing their impermeability over time.

In other or combined embodiments a replacement heart valve prosthesis as disclosed herein can be characterized in that a back flow can be achieved by way of back flow means, wherein said back flow means are spacers placed between the valve leaflets of the prosthesis, or between the prosthesis and the target tissue, and an area of the frame having two shape positions which in a variation can be changed in shape.

Moreover it is possible that a replacement heart valve prosthesis as disclosed herein can be characterized in that a back flow means is positioned between the prosthesis and the endogenous tissue of the target site, on or in the sealing means, in the valve, e.g. in the leaflets of the valve or between the leaflets, or between the sealing means and the valve.

The means to allow for a defined leakage and thus for a systolic backflow can be holes, gaps, cuts, etc. of from 0.5 mm to 5 mm in diameter. In another variation it can be one or more spacer of from 20 mm to 250 mm wherein the design of the spacer allows for a backflow between a spacer and a leaflet or a spacer and endogenous tissue of the heart.

Furthermore, the disclosure relates to a heart valve prosthesis as disclosed herein can be characterized in that the decrease or increase of back flow is achieved by way of active closing or opening of the back flow means, catheter-based implantation or removal of back flow means (e.g. spacer), systemic injection or local injection to the sealing means and/or replacement valve tissue of chemical substances which are capable of changing the impermeability thereof, chemical compounds accelerating or slowing natural ingrowth of tissue of the target tissue into the replacement heart valve, choosing biodegradable materials which lead to a closing of opening due to back flow means, back flow means are positioned in the replacement heart valve close to the target tissue (and thus ingrowth of natural tissue will reduce back flow and eventually completely block back flow), the back flow means are coated with growth factors or chemicals promoting cell attachment and/or cell growth, the back flow means are coated with cells leading to a sealing of the back flow means in vivo after implantation (e.g. a 70% sealing rate after 10 to 20 days, a 80% closure after 20 to 30 days, a 90% after 30 to 40 days, a 95% to 100% sealing rate at 50 days upon implantation in a patient or to change over a time window of from 1 to 12 weeks, or up to 10, 8, or 6 weeks. During this time frame the blood back flow will gradually reduce and eventually arrive at an essentially tight status in the steps of e.g. from torrential to severe or to moderate, or from severe to mild or to trace, or from moderate to mild or to trace or essentially tight).

It may also be possible to implant with the heart valve prosthesis a balloon which may minimally invasive be reconnected with a catheter when is appropriate and its pressure or volume and thus its diameter may be controlled and changed as is convenient and appropriate to define a specific degree of blood back flow. In this manner the degree of leakage can be controlled e.g. from torrential to severe or to moderate, or from severe to mild or to trace, or from moderate to mild or to trace or essentially tight. The balloon can be kept in the patient as long as is necessary to gradually reduce the blood back flow. After a time frame of 1 to 12 weeks the balloon can be removed and the heart valve prosthesis can continue to function normally. IT is also foreseeable that a certain catheter part remains connected with the balloon and can be operated as is necessary over a defined time frame.

The above can be combined with all known stent designs and it is anticipated that braided, laser cut, on, two, three, or multiple part stents are useful for such a defined leakiness.

In another aspect the disclosure relates to a method for changing minimally invasive or catheter-based the back flow rate in a replacement heart valve prosthesis wherein back flow means are manipulated to increase or to decrease the back flow rate.

In such a method the back flow means can be closed or opened, or reduced or increased, or implanted or removed.

In a method as disclosed herein the back flow means can be selected from biodegradable materials, materials changing their impermeability over time, or mechanical means to allow a defined blood back flow.

Further aspects of the disclosure of medical devices and methods are described in the following.

In one aspect the device according to the disclosure is a heart valve prosthesis which comprises one or more means to allow a defined blood back flow when the valve of the heart valve prosthesis is in its closed position, i.e. a perfect valve would not allow any back flow of blood due to the construction and design of the heart valve prosthesis including the valve component(s) and the valve. Thus a defined backwards flow of blood will occur and thus the pressure with regards to the replaced native heart valve will remain below a pressures achieved with a perfectly or essentially perfectly functioning heart valve prosthesis upon implantation. Such a defined leakiness will according to the disclosure reduce or it can be reduced over time in a defined manner, and after a defined time window there remains essentially no backflow in the heart valve prosthesis. Thus one can reduce for the patient and the patient's heart unwanted side effects linked to a change in the heart pressure conditions from diseased to treated which may imply side effects due to the new heart valve prosthesis, e.g. in the mitral or tricuspid heart valve and in the cause of a mitral or tricuspid heart valve replacement therapy.

In one aspect thus the disclosure is a heart valve prosthesis comprising a frame, a replacement valve and sealing means wherein the prosthesis has an inflow end and an outflow end and the inflow end and the outflow of the prosthesis form a conduit and wherein the valve leaflets open when a fluid enters into the in inflow end to allow the fluid to flow through the conduit (forward direction/forward valve flow) and the valve closes when a fluid flows into the outflow end to prevent the fluid to flow through the conduit (reverse direction/backwards valve flow or back valve flow) characterized by a defined amount of a blood backwards flow in the reverse direction/backwards flow when the valve leaflets are closing or closed.

The leakiness can be defined according to the needs of the medical circumstances and the patient's condition. Thus in the heart valve prosthesis according to the disclosure and as described above the defined amount of blood backwards flow in the reverse direction is predefined or it varies over time, e.g. it decreases or increases over a defined time frame, wherein the defined time frame is 1 day to 90 days or/and the blood backwards flow can be a valve backwards flow or/and it can be a blood backwards flow outside the heart valve prosthesis or/and between the heart valve prosthesis and the native heart valve or the surrounding valve tissue.

Depending on the native heart valve to be replaced, e.g. mitral or tricuspid, a prosthesis according to the disclosure the blood backwards flow is a systolic or diastolic blood backwards flow; one may chose a blood backwards flow of e.g. 5 to 40% of the outflow (forward outflow). The means to define and design the blood backwards flow may be e.g. a limited closing of valve leaflets of the heart valve prosthesis, or at the valve leaflets themselves, or a means between the heart valve prosthesis and the surrounding tissue, e.g. a spacer, or a means between the valve leaflets themselves.

On the one hand in a diseased person may be grouped or the severity of the malfunctioning heart valve can be characterized according to a scale. On the other hand the replacement heart valve itself can also be defined in such a manner depending on the blood backwards flow it allows. Heart valve prosthesis according to the disclosure can thus exhibit a systolic or diastolic blood backwards flow which can be characterized as severe, moderate, mild, or trace.

A backwards flow can be achieved by any useful manner wherein the backwards flow can be defined in its level and also in that e.g. a defined reduction in backwards flow will be defined. In a heart valve prosthesis according to the disclosure can be characterized wherein a blood backwards flow can be achieved by way of blood backwards flow means, wherein said backwards flow means is selected from the group consisting of active opening means, e.g. filters, flaps, spacers, valves, and passive opening means, e.g. holes, cuts, openings located at any sealing surface of the prosthesis.

In a heart valve prosthesis according to the disclosure a backwards flow can be achieved e.g. by way of backwards flow means, wherein said backwards flow means are selected from biodegradable materials, materials changing their impermeability over time. Such a material can also be chosen from a material which is degrading within the body of an individual within a time frame of 4 to 12 weeks and is dissolved essentially entirely by the body. In such a way it will reduce its diameter if it is formed e.g. as a ring around the heart valve prosthesis on the outside surface or single biodegradable means at a position outside the heart valve prosthesis in the area of the annulus or at various levels outside the heart valve prosthesis will allow for a defined amount of blood backflow. Over time the diameter of volume will degrease and thus the heart valve prosthesis will by its natural tendency to axially expand align with the surrounding tissue and thus the predefined leakage will reduce in amount and thus it will reduce the blood backflow over the predefined time frame like 2 to 16 week or 2 to 8 week or any other useful time frame.

A heart valve prosthesis according to the disclosure can exhibit a backwards flow which can be achieved by way of blood backwards flow means, wherein said backwards flow means are spacers placed between the valve leaflets of the prosthesis, or between the prosthesis and the target tissue, and an area of the frame having two shape positions which can be switched from one to the other one during implantation.

A heart valve prosthesis according to any the disclosure can be characterized in one aspect wherein the blood backwards flow means are positioned between the prosthesis and the endogenous tissue of the target site, on or in the sealing means, in the valve, e.g. in the leaflets of the valve or between the leaflets, or between the sealing means and the valve.

A heart valve prosthesis according to the disclosure can be characterized wherein the decrease or increase of backwards flow is achieved by way of active closing or opening of the blood backwards flow means, catheter-based implantation or removal of backwards flow means (e.g. spacer), systemic injection or local injection to the sealing means and/or replacement valve tissue of chemical substances which are capable of changing the impermeability thereof, chemical compounds accelerating or slowing natural ingrowth of tissue of the target tissue into the replacement heart valve, choosing biodegradable materials which lead to a closing of opening due to backwards flow means, backwards flow means are positioned in the replacement heart valve close to the target tissue (and thus ingrowth of natural tissue will reduce backwards flow and eventually completely block backwards flow), the backwards flow means are coated with growth factors or chemicals promoting cell attachment and/or cell growth, the backwards flow means are coated with cells leading to a sealing of the backwards flow means in vivo after implantation (e.g. a 70% sealing rate after 10 to 20 days, a 80% closure after 20 to 30 days, a 90% after 30 to 40 days, a 95% to 100% sealing rate at 50 days upon implantation in a patient).

In another aspect the disclosure relates to a method for changing minimally invasive or catheter-based the blood backwards flow rate in a replacement heart valve prosthesis wherein backwards flow means are manipulated to increase or to decrease the backwards flow rate.

The method according to the disclosure and as described herein can be characterized wherein the blood backwards flow means are closed or opened, or reduced or increased, or implanted or removed.

In a variation of the method according to the disclosure the blood backwards flow means are selected from biodegradable materials, materials changing their impermeability over time.

REFERENCE NUMBERS

101 Heart valve prosthesis
102 Spacer/balloon

103 Flaps
104 Filter/valve
105 Cuts/slots
106 Holes
107 Heart muscle
108 Biodegradable ring

What is claimed is:

1. A heart valve prosthesis comprising:
a frame,
a replacement valve and
a sealing means;
wherein the prosthesis has a first end and a second end and the first and second ends of the prosthesis form a conduit and wherein valve leaflets open when a fluid enters into the first end to allow the fluid to flow through the conduit in a forward direction and the valve closes when a fluid flows into the second end to prevent the fluid to flow through the conduit in a reverse direction, wherein flow through the conduit in the forward direction is a forward valve flow, characterized by an initial defined amount of a blood backwards flow in the reverse direction of about 5 to about 40 percent of the forward valve flow when the valve leaflets are closed;
wherein the heart valve prothesis is configured so that the amount of blood backward flow in the reverse direction decreases over a defined time frame of 1 to 90 days.

2. The heart valve prosthesis according to claim 1, wherein the blood backwards flow:
is a valve backwards flow, or
is a blood backwards flow outside the heart valve prosthesis, or
is a blood backwards flow between the heart valve prosthesis and the native heart valve or the surrounding valve tissue.

3. The heart valve prosthesis according to claim 1, wherein the blood backwards flow is a systolic or diastolic blood backwards flow:
with limited closing of valve leaflets of the heart valve prosthesis, or
at the valve leaflets, optionally with a spacer, or
between the valve leaflets.

4. The heart valve prosthesis according to claim 3 wherein the systolic or diastolic blood backwards flow can be characterized as severe, moderate, mild, or trace.

5. The heart valve prosthesis of claim 1, wherein a blood backwards flow can be achieved by way of blood backwards flow means, wherein said backwards flow means are active opening means or passive opening means, wherein the active opening means, optionally includes filters, flaps, spacers, valves, and the passive opening means optionally includes holes, cuts, openings located at any sealing surface of the prosthesis.

6. The heart valve prosthesis of claim 1, wherein a backwards flow is achieved by way of backwards flow means, wherein said backwards flow means includes biodegradable materials or materials changing their impermeability over time.

7. The heart valve prosthesis of claim 1, wherein a backwards flow can be achieved by way of blood backwards flow means, wherein said backwards flow means are spacers placed between the valve leaflets of the prosthesis, or between the prosthesis and the target tissue, and an area of the frame having two shape positions which can be switched from one of the two shape positions to the other of the two shape positions during implantation.

8. The heart valve prosthesis of claim 1, wherein the blood backwards flow means are positioned between the prosthesis and the endogenous tissue of the target site, on or in the sealing means, in the valve, or between the sealing means and the valve.

9. The heart valve prosthesis of claim 1, wherein the decrease or increase of backwards flow is achieved by way of active closing or opening of the blood backwards flow means, catheter-based implantation or removal of backwards flow means, systemic injection or local injection to the sealing means and/or replacement valve tissue of chemical substances which are capable of changing the impermeability thereof, chemical compounds accelerating or slowing natural ingrowth of tissue of the target tissue into the replacement heart valve, choosing biodegradable materials which lead to a closing of opening due to backwards flow means, the backwards flow means are coated with growth factors or chemicals promoting cell attachment and/or cell growth, the backwards flow means are coated with cells leading to a sealing of the backwards flow means in vivo after implantation.

10. The heart valve prosthesis of claim 1, wherein the blood backwards flow is a valve backwards flow.

11. The heart valve prosthesis of claim 1, wherein the blood backward flow is a blood backwards flow outside the heart valve prosthesis.

12. The heart valve prosthesis of claim 1, wherein the blood backward flow is between the heart valve prosthesis and the native heart valve or the surrounding valve tissue.

13. The heart valve prosthesis of claim 1, wherein a blood backwards flow is achieved by way of blood backwards flow means, wherein said backwards flow means are selected from the group consisting of active opening means, and passive opening means, wherein the active opening means is selected from the group consisting of filters, flaps, spacers, and valves, and passive opening means is selected from the group consisting of holes, cuts, and openings located at any sealing surface of the prosthesis.

14. The heart valve prosthesis of claim 13, wherein the backwards flow means includes a biodegradable material.

15. The heart valve prosthesis according to claim 1, wherein the heart valve prosthesis includes:
   i) spacers that are removable for reducing the blood backward flow over time; or
   ii) a part that closes automatically over time for reducing the blood backward flow over time; or
   iii) a biodegradable conduit for the blood backward flow, wherein the degradation of the conduit reduces the blood backward flow over time; or
   iv) an opening for blood backward flow, wherein the opening is arranged to promote a natural tissue ingrowth for closing the opening and reducing the blood backward flow over time; or
   v) an opening coated with a growth factor or chemical for promoting cell attachment and/or cell growth for reducing blood backward flow over time; or
   vi) a mechanical means for reducing blood backward flow over time; or
   vii) a biodegradable ring on an outside surface of the prosthesis for reducing blood backward flow over time; or
   viii) a balloon, wherein a volume of the balloon is controllable for reducing blood backward flow over time.

* * * * *